(12) United States Patent
King

(10) Patent No.: US 11,980,533 B2
(45) Date of Patent: May 14, 2024

(54) DISCRETE DEVICE AND METHOD FOR FEMININE HYGIENE

(71) Applicant: Steven King, Solana Beach, CA (US)

(72) Inventor: Steven King, Solana Beach, CA (US)

(*) Notice: Subject to any disclaimer, the term of this patent is extended or adjusted under 35 U.S.C. 154(b) by 623 days.

(21) Appl. No.: 17/208,319

(22) Filed: Mar. 22, 2021

(65) Prior Publication Data

US 2022/0071819 A1 Mar. 10, 2022

Related U.S. Application Data

(60) Provisional application No. 62/992,662, filed on Mar. 20, 2020.

(51) Int. Cl.
| | |
|---|---|
| *A61F 13/551* | (2006.01) |
| *A45C 11/00* | (2006.01) |
| *G06N 5/02* | (2023.01) |
| *G16H 10/60* | (2018.01) |
| *G16H 40/20* | (2018.01) |
| *G16H 40/40* | (2018.01) |
| *G16H 40/67* | (2018.01) |
| *H04L 43/16* | (2022.01) |

(52) U.S. Cl.
CPC ......... *A61F 13/55175* (2013.01); *G06N 5/02* (2013.01); *G16H 10/60* (2018.01); *G16H 40/20* (2018.01); *G16H 40/40* (2018.01); *G16H 40/67* (2018.01); *A45C 2011/007* (2013.01); *H04L 43/16* (2013.01)

(58) Field of Classification Search
CPC .............. A45C 11/00; A45C 2011/007; A61F 13/55175; G06N 5/02; G16H 10/60; G16H 40/20; G16H 40/40; G16H 40/67; H04W 4/023; H04L 43/16
See application file for complete search history.

(56) References Cited

U.S. PATENT DOCUMENTS

| | | | |
|---|---|---|---|
| 2016/0328813 A1* | 11/2016 | Montgomery | G06Q 10/087 |
| 2016/0364686 A1* | 12/2016 | Wolfe | G16H 30/40 |
| 2021/0304122 A1* | 9/2021 | Dattamajumdar | G06T 7/74 |
| 2022/0083750 A1* | 3/2022 | Hussain | G06K 7/10168 |

* cited by examiner

*Primary Examiner* — Nguyen T Vo
(74) *Attorney, Agent, or Firm* — Donn K. Harms

(57) ABSTRACT

A feminine product carrier is configured to hold tampons and other products within individual recesses. Sensors monitoring occupancy of the recesses cause a graphic interface on a computing device of the user, such as a smartphone, to depict which of the plurality of recesses is occupied and which is empty. A transceiver engaged to the carrier will provide a graphic depiction of a location of the carrier and initiate a warning when the carrier is determined to be not proximate to the location of the user.

11 Claims, 2 Drawing Sheets

DISCRETE DEVICE AND METHOD FOR FEMININE HYGIENE

This application claims priority to U.S. Patent Application Ser. No. 62/992,662, filed on Mar. 20, 2021, which is incorporated herein in its entirety by this reference thereto.

BACKGROUND OF THE INVENTION

1. Field of the Invention

The invention herein disclosed relates generally to feminine hygiene and fertility. More particularly, it relates to a discrete tampon and cosmetic carrying device employing a system, enabled by computer executable code, to help users maintain a timely supply of feminine products and to track both menstrual and fertility cycles.

2. Prior Art

With the advent of modern feminine hygiene, women widely use tampons during their menstrual cycle. Such tampon devices are compact and easily carried by most women in a purse or the like.

However, women over the days of a month, have many responsibilities in a modern society on which they must focus their attention. Working women have responsibilities, daily, which must be met and accomplished. Consequently, they may not be overly focused on their monthly cycle which requires the use of feminine hygiene products such as tampons.

As a consequence of such busy schedules and the plethora of responsibilities of modern women, it can be easy to overlook the need to carry their feminine hygiene products in their purse or on their person on the actual days they become a requirement. Such a lack of focus on the date and need for hygiene products is not a memory issue, but is of course a result of having to continuously think about and juggle and perform the multiple responsibilities of work and home.

As such, it is not uncommon for women to be caught off guard and not have required products with them when the need arises. Further, even when such products are kept readily available in a case or holder for carrying on their person, on the appropriate days, they are easily forgotten at home when rushing to start daily responsibilities.

With respect to the above, before explaining at least one preferred embodiment of the feminine hygiene system herein, it is to be understood that the system invention is not limited in its application to the details of employment and to the arrangement of the components or the steps set forth in the following description or illustrated in the drawings. The various apparatus and methods and steps of the herein disclosed feminine product system is capable of other embodiments, and of being practiced and carried out in various ways, all of which will be obvious to those skilled in the art once the information herein is reviewed.

Also, it is to be understood that the phraseology and terminology employed herein are for the purpose of description and should not be regarded as limiting. As such, those skilled in the art will appreciate that the conception upon which this disclosure is based may readily be utilized as a basis for other feminine hygiene carrying and reminder systems. It is important, therefore, that the embodiments, objects and claims herein, be regarded as including such equivalent construction and methodology insofar as they do not depart from the spirit and scope of the present invention.

SUMMARY OF THE INVENTION

The disclosed system herein, provides a feminine hygiene and cosmetic product carrier which is configured to communicate with a computing device such as a cell phone or portable computer. The product carrier employing wireless communications with the user computing device running software adapted to the task, is configured to provide the user updates concerning the supply of needed products currently held in the carrier.

Additionally, the system employing computer actuable code running on the wirelessly linked portable computer of the user having electronic memory and wireless communication components, is configured to the task of initiating alarms or other "pushed" notifications of both the need to have the carrier in their possession on days during the month where it should be with the user. In some modes the device and system also provide the user the ability to order needed products and have them timely delivered.

Still further, the carrier can be configured to hold both feminine hygiene products, and other products such as cosmetics or the like, in user chosen sections thereof. So configured, the system employing computer software or executable code configured to the described tasks, will continuously take inventory and track monthly dates and operate to remind and inform the user of the remaining supply of each product within the carrier.

The reminder system, using a time of day and/or GPS or other geo-locators to determine a system location, can make certain that on the days required, the user is reminded to place the carrier on their person, before they depart to a remote location from their home. Additionally, the system can be interactive with the user to supply them with needed information concerning health, or in one mode fertility, should such be desired.

Finally, computer executable code or a software application is provided to run in electronic memory of a user owned computing device such as a smart phone, which will provide the user with updates, warnings, and product ordering suggestions, based on user use history which is tracked over time. Further, icons on the graphic interface in operative communication with the computer can be provided to allow the user to order needed products from the system provider, as well as request health information and suggestions therefrom.

With respect to the above description, before explaining at least one preferred embodiment of the feminine hygiene carrier and system herein, it is to be understood that the invention is not limited in its application to the details of operation nor the arrangement of the components or the steps set forth in the following description or illustrations in the drawings. The various methods of implementation and operation of the method herein are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

Therefore, those skilled in the art will appreciate that the conception upon which this disclosure is based may readily be utilized as a basis for designing of other methods and systems for carrying out the several purposes of the present method. Therefore, that the objects and claims herein should be regarded as including such equivalent construction, steps, and methodology insofar as they do not depart from the spirit and scope of the present invention.

It is an object of this invention to provide a system for reminding users to have a system-enabled carrier for feminine products on their person on days of the month when it may be needed.

It is a further object of this invention to alarm the user should they have the carrier properly loaded with needed products, but forget to place it back in their purse or on their person when moving to another location.

These together with other objects and advantages which become subsequently apparent reside in the details of the construction and operation of the system herein as more fully hereinafter described and claimed, reference being had to the accompanying drawings forming a part thereof, wherein like numerals refer to like parts throughout.

Further objectives of this invention will be ascertained by those skilled in the art as brought out in the following part of the specification wherein detailed description is for the purpose of fully disclosing the invention without placing limitations thereon.

BRIEF DESCRIPTION OF DRAWING FIGURE

Figure 1:
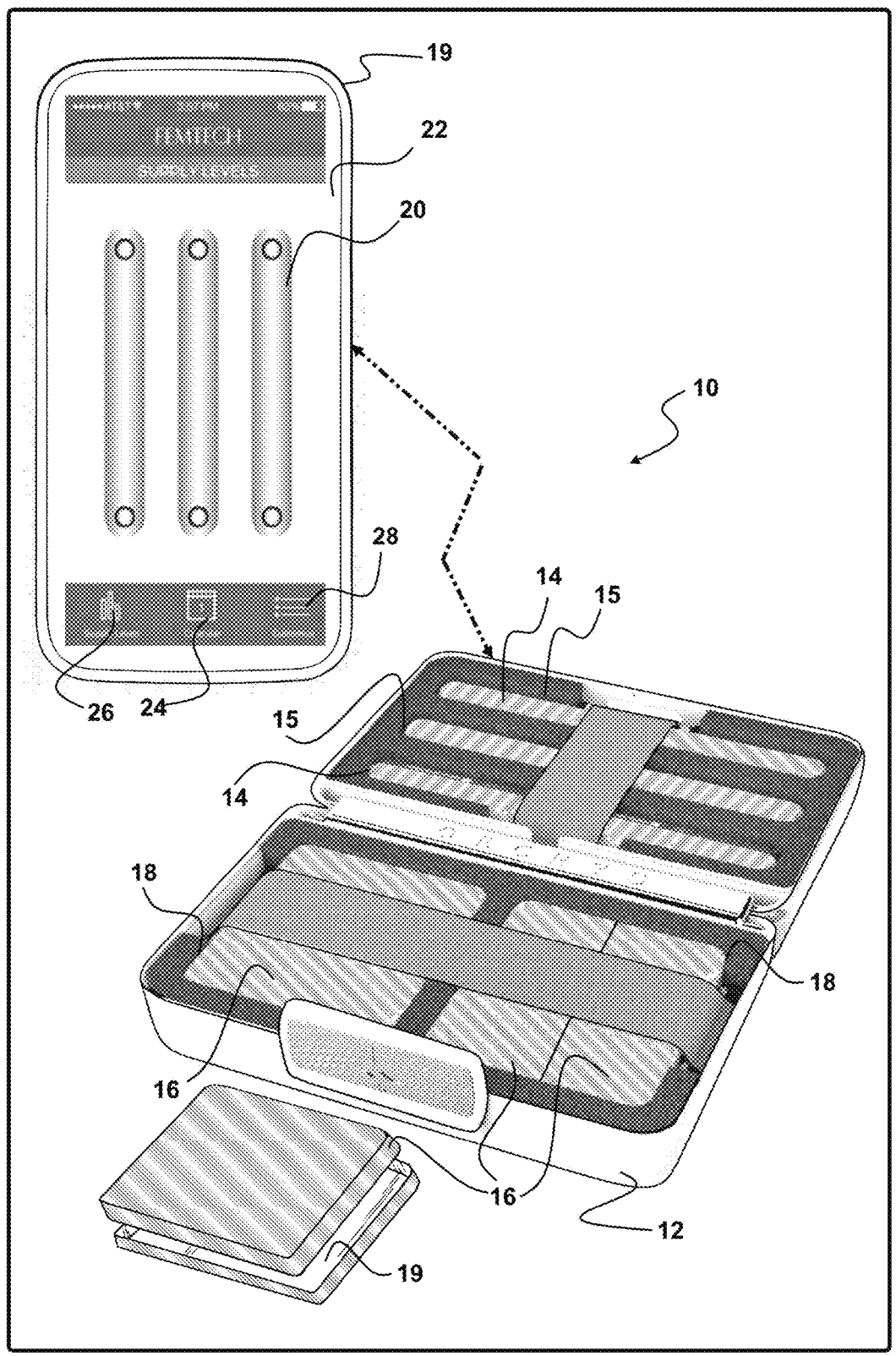
FIG. 1 depicts components of the system herein showing a carrier configured to hold tampons and to hold user configurable containers and depicting the wireless communication between the carrier and a cell phone having a graphic interface depicting the current contents of the carrier for the user.
Figure 2:
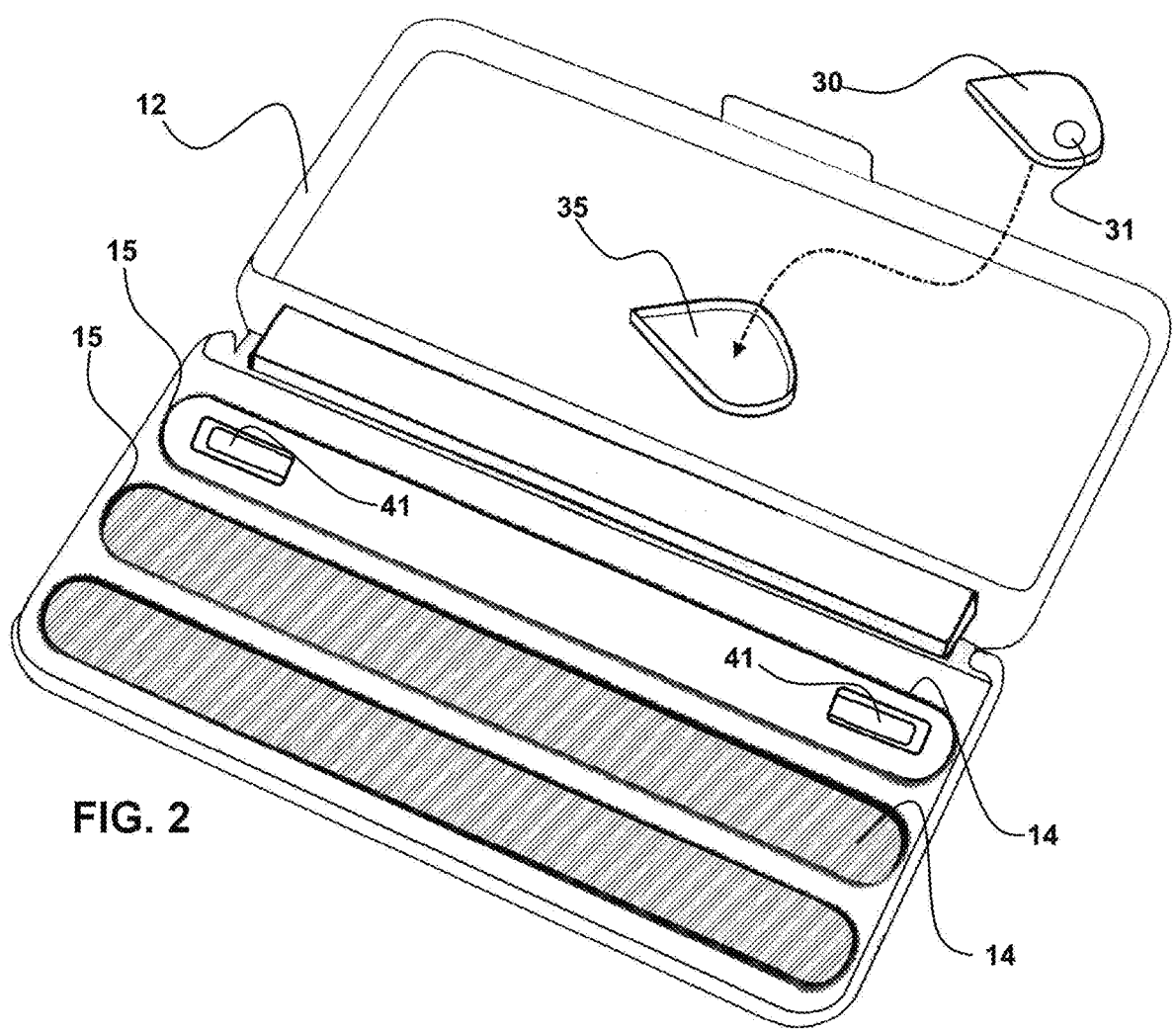
FIG. 2 shows another mode of the carrier having tampon recess locations each of which have recess sensors shown as contact switches engaged therewith to determine the contents of each location, and showing an optional transceiver interface which is engageable with the carrier to provide a secure interface as well as a location beacon.
Figure 3:
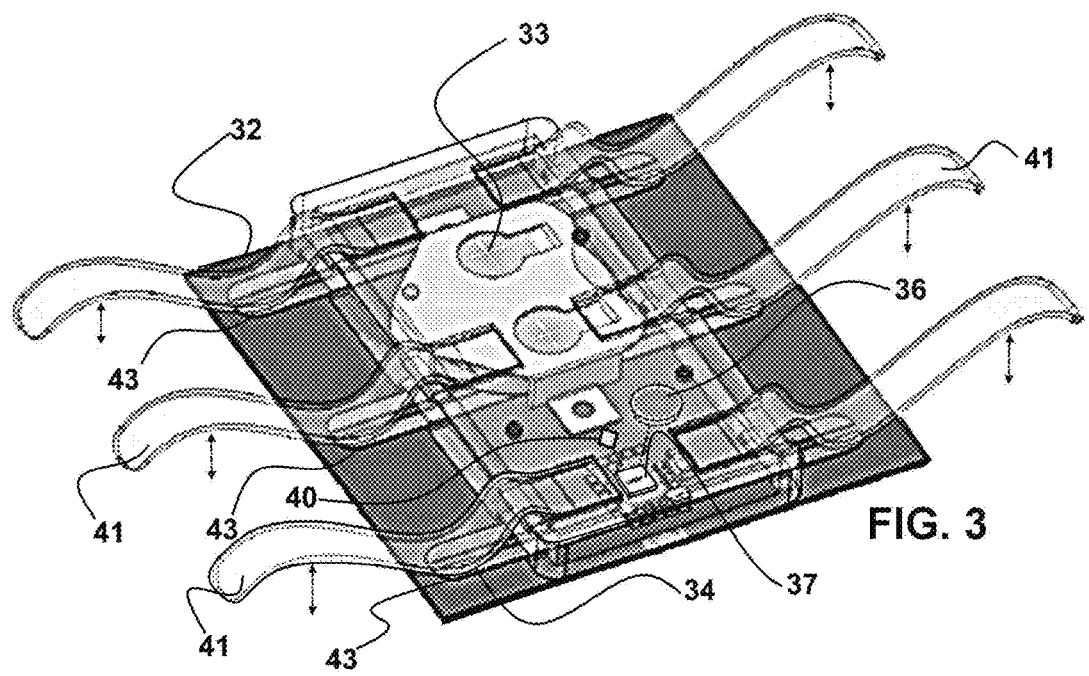

FIG. 3 depicts a configuration of a switching component which is positioned within the devices of FIG. 1 or FIG. 2, showing the recess sensors configured to detect the presence of tampons within each recess and having a computer controller and operatively engaged components configured to cause that controller to communicate with the computer device of the user, to provide a visually discernable assessment of the current carrier contents and location between the carrier and computer device.

DETAILED DESCRIPTION OF THE PREFERRED EMBODIMENTS OF THE INVENTION

Referring now to the system herein, shown in simple format by the depictions of FIGS. 1-3, it should be noted that in all modes of the system 10 herein, the carrier 12 is enabled with a computer processor 37 (FIG. 3) in operative engagement to electronic memory able to run computer executable code or software, is configured run to perform the individual tasks such as each noted task of sensing and communicating with the user computer device 29 such as a smartphone. The processor 37 is also in operative communication with recess sensors 34 configured to sense the positioning of contents in recesses 15 in the carrier 12 and to report contents such as a tampon 14 occupying a recess 15, or lack thereof. The sensors 34 provide a signal to the controller 32 that a tampon 14 is currently positioned in a recess 15 or that the recess 15 is empty, in real time so that such can be depicted on the graphic interface 20. Geographic position sensors 40, using GPS signals and/or cell tower signal triangulation, operate to determine and report a position of the carrier 12 to the user computing device 17.

As shown in FIG. 1 and in FIG. 2, the provided carrier 12 has a plurality of recesses 15 which are dimensioned for positioning of one tampon 14 in each individual tampon recess 15. By dimensioned is meant that the recess 15 is of a length and width which allows for the positioning of a tampon 14 having an equal or smaller length and width to that of the recess 15 therein. Preferably the recess 15 has a diameter which is slightly smaller than the diameter of an inserted tampon 14 to thereby engaged the tampon 14 within the recess in a biased contact therewith since the tampon 14 will compress along the longitudinal axis to fit in the narrow width recess 15.

The carrier 12 can be configured solely to hold tampons 14 as in FIG. 2, or can be configured to hold tampons 14 in individual recesses 15 within the carrier 12 as well as user-chosen containers shown as pods 16. The pods 16 are hollow holders having a respective interior cavity 19 therein shown in the cutout in FIG. 2, which may be accessed by removing or opening a top cover 21 which is frictionally, or otherwise engaged. The internal cavity 19 is configured for positioning of user-chosen cosmetic and sanitary items therein, such as makeup or cleaning wipes or other user-chosen contents.

The pods 16 will preferably have the same maximum external dimensions which are all adapted for positioning within a pod recess 18 before closing of the carrier 12 for storage and transport during the day. The pods 16 can have thinner dimensions allowing stacking of multiple pods 16 within an individual pod recess 18 or can be formed in half sizes where two smaller pods 16 fill an individual pod recess 18. In this fashion, the user can have a collection of pods 16 which have interior cavities 19 which are loaded with different items the user may wish to carry on different days, thereby allowing the user the ability to pre load pods in the collection and insert the desired pods 16 into the pod recesses 18 in anticipation of their needs for the upcoming day.

Also shown in FIG. 1, the graphic interface 20 which will appear on the computer display 22 of the computing device 17 of the user, such as a smart phone, smart watch, or pad computer. The graphic interface 20 software will be provided to the user by download over a network from the system 10 provider or on an electronic memory device such as a thumb drive and will be installed on the user computer device 17 by the user. Once installed and operating in electronic memory of the user device 17, the graphic interface 20 in operative communication with the computer and electronic memory on the user device 17, will display to the user the current contents of the tampon recesses 15 and/or the pod recesses 18, thereby informing them as to whether they need to reload the carrier 12. Particularly preferred on the graphic interface 20, are graphic depictions 27 of each of the individual recesses 15 within the carrier 12, where the depiction 27 will be one color such as green where the represented recess 15 is occupied, and a second color such as red where the depicted respective recess 15 is empty.

Additionally provided by the system 10 is computer executable code in the form of a calendaring software application which operates computer executable instructions which, to elicit date responses from the user upon a first activation thereof which occurs when the user touches the calendar icon 24. The calendaring software will then elicit specific date responses from the user as to their menstrual cycle. Based on the user input, the calendaring software will employ computer executable code or the calendaring software running on the user computing device 17, to track both the menstrual cycle of the user, as well as the estimated fertility cycle of the user.

The computer executable code for the calendaring software application can be loaded to electronic memory of the computing device 17 of the user by downloading such from the system provider networked website or can be provided on a disk or electronic memory component provided with the carrier 12. The calendaring software will employ computer executable code to store the user input concerning menstrual cycle and optionally to use stored information allowing a prediction of the fertility cycle of the user, based on their input to the questions concerning menstrual cycle. Such predictive information is well known based on the date of the start of the user menstrual cycle and easily stored in electronic memory to allow the calendaring software to provide such a calculation and prediction.

Additional functions of the software running on the user computing device 17 which employs computer executable code configured to the appropriate task can also include product ordering software using computer executable instructions which will be depicted on the graphic interface 20 of the computer display 22, to ask if the user wishes to order more products. The depicted instructions would instruct the user to touch and employ a depicted ordering icon 26, to initiate an order of product from a vendor such as AMAZON or another online product vendor.

Additionally provided, the system provider can also include upon the graphic interface 22 other user executable icons 28, which when activated by touch, will enable the user to seek more information concerning their health and other information related thereto.

Using the network communication components and computer executable code of the software running upon the user computer 17 device, the products and/or information requested by a user can be wirelessly communicated from the user computing device 17 in a network communication with the server or computer of the system provider which is configured to interface with each such user and their respective user computing device 17. Network communication, such as by a WiFi connection, or a cellular phone connection, is well known for user devices 17 such as smartphones and tablet computers and thus need not be explained in detail.

Because each of such networked user computing device 17 has a MAC ID or identifier which is unique to that individual user computing device 17, the system provider computer or server will, once the user has installed the graphic interface software, store the identifier or MacID of each respective user in a relational database and automatically ascertain the identity of the respective individual user on subsequent communications, based on this MAC ID. This is done for each network communication by software having computer executable code configured to lookup the user based on their computer identifier such as its MAC ID, which have been correlated to identify individual users of a user computing device 17 having such. Alternatively, or in combination with the communicated MAC ID, which is captured upon user registration with the system provider, a unique user identifier and password can also provide means to identify the individual user for provision of requested information or shipment of requested products thereto.

Shown in FIG. 2, is another preferred mode of the carrier 12 of the system 10 herein. As shown, the carrier 12 is configured with individual tampon recesses 15 and can also be configured as in FIG. 1, to also include individual pod recesses 18 to allow the user to pack and insert pods 16 of choice into such. Thus, the carrier 12 of FIG. 2 is illustrative only and could be formed to other shapes and with differing recesses for both pods 16 and tampons 14 and the like.

Additionally shown in FIG. 2, and employable in all modes of the carriers 12 of the system 10 herein, is a proximity transceiver 30 which is removably engageable to a transceiver recess 35 positioned somewhere on the carrier 12. The proximity transceiver 30, using WiFi, Bluetooth, or other wireless communication, is programmed to wirelessly communicate with the user computing device 17 and provide a proximity warning to the user, if the carrier 12 becomes located a distance determined as too far from the user computer 17 device.

This proximity warning is provided by a blue tooth or other response wireless transmission emitted by the battery powered transceiver 30. The response wireless transmission is generated in response to a query signal initiated in a first task by proximity software running on the user computing device 17 and broadcast by the wireless transmitter on the user computing device 17 which as noted is well known on smart phones and pad or tablet computing devices.

This proximity software running in memory of the user computing device 17 in a second task, upon receipt of the response wireless transmission from the transceiver 30, operates to calculate a determined carrier location of said carrier relative to a location of said user computing device from the signal strength, or duration of time taken for the wireless response transmission from the transceiver. Such a signal strength or duration of time for each response transmission generated from a query signal is employed by the proximity software running on the user computing device 17 of the user to determine a distance of the carrier from the user computing device as a current carrier location.

In a third task of the proximity software running on the user computing device, said proximity software will operate to the task of generating a carrier location depiction on said user graphic interface based on said determined carrier location. Should the carrier location calculated be a distance exceeding a predetermined maximum which can be set by the user or by default, a warning indication that the user has forgotten to take the carrier 12 with can be generated by the proximity software running on the user computing device in a fourth task thereof. On such an occurrence the proximity software will operate to cause the graphic interface 20 to visually depict a warning, such as text or an icon, that the user has forgotten the carrier 12, and/or will initiate an audio signal using the speaker of the user computing device 17 of the user to do so.

The proximity transceiver 30 can act as a carrier locator in such instances where the user cannot discern where they have left the carrier 12. The proximity transceiver 30, using an onboard transducer 31 such as a beeper or the like, can be actuated by a wireless signal from the user computing device 17. Using locating software running on the computing device of the user which is activated by the user touching an icon on the graphic interface 20 or a spot thereon, which is generated by the locating software running to the task of locating the carrier for the user. Such will activate the locating software of the system 10 running on the user computing device 17, send a secondary query signal to cause the transceiver to sound an audible signal from the transducer 31. Using the audible signal from the transducer 31, the user can then locate the carrier 12 from the sound.

The proximity transceiver 30 can be included in any or all of the carriers 12 of the system 10 herein. Alternatively, computer executable code running on the user computing device 17 in the form of mapping software, can generate a virtual map upon the graphic interface 20. The depicted virtual map can show a calculated current location of the computing device 17 of the user and that of the location transceiver 30 engaged with the carrier 12, to allow the user to use the graphic interface 20 to follow it to the depicted location of the carrier 12 thereon. This will work well when the carrier 12 and engaged proximity transceiver 30 is out of an audible range for the user to hear the sound of the transducer 31. The calculation of the two locations would be determined using the computer executable code of the mapping software to calculate a distance of the proximity transceiver 30 from the user computing device 17 and a direction to the proximity transceiver 30 based on the wireless signal strength of transmissions therefrom as the user computing device 17 is moved.

Shown in FIG. 3, is an example of a controller 32 which is battery 33 powered and is operatively positioned within a carrier 12. As shown, the controller 32 has a plurality of sensors 34 which act as contact switches. Each contact switch has an elongated first contact 41 which is biased upward and projects through an opening into each of the recesses 15 as shown in FIG. 2. In this upward biased positioning, the first contact 41 is separated and out of contact with the second contact 43 of the switch forming the sensor 34 when the recess 15 is empty since there is no tampon therein to deflect the upward biased first contact 41 to move downward and come into contact with the second contact to close the circuit.

Thus, when the monitored recess 15 is not loaded with a tampon, the sensors 34 switch open which will not generate a signal to the controller that recess 15 is occupied. When a tampon is located in a respective recess 15 it will cause one or both switches formed by first contacts 41 and second contacts 43 to close by deflecting the first contact 41 to touch the second contact 43. This closed circuit will cause an electric signal such as from the operatively engaged battery 33, or one which is sensed by an input on the controller for a resistance or capacitance signal, which will cause the controller using software running thereon to activate a wireless transmitter 36. So activated the transmitter 36 will communicate a signal to the user computing device 17 of the user, which one of the respective monitored recess 15 or 18 are occupied and have closed the switch contact and which is empty and needs replenishment.

Of course, the first contact 41 and second contact 43 forming the current sensors 34, while shown as mechanical switches, could be any sensor which will send an appropriate signal to the processor 37 on the controller 32 concerning the current status of a recess 15 or 18, such as a light emitter and receiver or other sensor as would occur to those in the art. However, currently it has been found in experimentation that using the spring loaded first contact 41 separated from the second contact 43, is very reliable and especially resistant to damage from hard impacts such as dropping the device 10 and such are preferred for durability. Additionally, because on occasion tampons may be compressed or otherwise misaligned with the recesses 15, two sensors or switches such as formed of the first contact 41 and second contact 43, with one at each end of each recess 15, has shown to be especially reliable against producing false empty alarms.

In all modes of the system 10 herein, the system provider will employ a computer or server in communication with electronic memory and in operational communication over a network such as the internet, which is accessible for bidirectional communications with and between each respective computing device 17 of each user. The system provider will employ one or a plurality of computing devices such as a computer or server, having electronic memory in which computer executable code for each type of software noted herein will perform the steps and the tasks noted herein, such as the ordering products by users from their respective user computing devices 17, and the provision of requested health or other information to users.

While all of the fundamental characteristics and features of the system for carrying, ordering, and reminding users concerning the need for feminine hygiene and cosmetic products been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A feminine product transport apparatus comprising:
   graphic depiction software operating on a computer device of a user, said graphic depiction software operating to generate a user graphic interface on a display of said computer device of said user;
   a carrier, said carrier having a plurality of recesses positioned therein;
   a controller positioned on said carrier, said controller having an onboard power supply and having a computer processor and electronic memory operatively connected thereto;
   said controller having a wireless transmitter operatively engaged therewith;
   each of said recesses dimensioned for positioning of a tampon therein;
   each of said recesses having a respective sensor connected thereto;
   each respective sensor communicating a respective electronic occupancy signal to said controller only when a said tampon is located in the respective recess connected to said sensor;
   software running in said electronic memory of said controller operating to the task of transmitting said occupancy signal from said wireless transmitter to said computer device of said user;
   receipt of said occupancy signal by said graphic depiction software generating a recess depiction on said user graphic interface on said display of said user;
   said recess depiction showing each respective recess wherein said respective sensor connected therewith generated a said occupancy signal as a respective recess occupied by a tampon; and
   said recess depiction showing each respective recess wherein no occupancy signal was generated by said respective sensor connected therewith, as an empty respective recess.

2. The feminine product transport apparatus of claim 1, additionally comprising:
   a transceiver recess positioned on said carrier;
   a proximity transceiver, said proximity transceiver removably engaged to said transceiver recess;

proximity software running on said user computing device operating to a first task of emitting a query signal to said proximity receiver from a user device wireless transmitter;

said transceiver emitting a response wireless transmission in response to said query signal;

said proximity software operating to a second task of calculating a determined carrier location of said carrier relative to a location of said user computing device; and said proximity software operating to a third task of generating a carrier location depiction on said user graphic interface based on said determined carrier location.

3. The feminine product transport apparatus of claim 2, additionally comprising:

said proximity software running on the computing device of the user operating in a fourth task to generate a warning, said warning depicted on said graphic interface that said carrier has been forgotten when said determined carrier location exceeds a predetermined distance from said user computing device.

4. The feminine product transport apparatus of claim 3, additionally comprising:

said warning including an audible signal from a transducer located on said transceiver, said audible signal initiated by a wireless signal from said user computing device which is activated by said proximity software as a function of said fourth task.

5. The feminine product transport apparatus of claim 4, additionally comprising:

said sensor connected with each said recess is comprised of a first contact of a switch which projects into said recess and a second contact positioned within said carrier; and said occupancy signal generated only when a said tampon located in said recess deflects said first contact into electrical contact with said second contact.

6. The feminine product transport apparatus of claim 3, additionally comprising:

said sensor connected with each said recess is comprised of a first contact of a switch which projects into said recess and a second contact positioned within said carrier; and said occupancy signal generated only when a said tampon located in said recess deflects said first contact into electrical contact with said second contact.

7. The feminine product transport apparatus of claim 2, additionally comprising:

said sensor connected with each said recess is comprised of a first contact of a switch which projects into said recess and a second contact positioned within said carrier; and said occupancy signal generated only when a said tampon located in said recess deflects said first contact into electrical contact with said second contact.

8. The feminine product transport apparatus of claim 2, additionally comprising:

said sensor connected with each said recess is comprised of a first switch positioned at a first end of said recess and a second switch positioned at an opposite end of said recess;

said first switch having a first contact which projects into said recess and a second contact positioned within said carrier;

said second switch having a first contact which projects into said recess and a second contact positioned within said carrier; and said occupancy signal generated when a said tampon located in said recess deflects either said first contact of said first switch into a first electrical contact with said second contact of said first switch, or said first contact of said second switch into a second electrical contact with said second contact of said second switch.

9. The feminine product transport apparatus of claim 1, additionally comprising:

said sensor connected with each said recess is comprised of a first contact of a switch which projects into said recess and a second contact positioned within said carrier; and said occupancy signal generated only when a said tampon located in said recess deflects said first contact into electrical contact with said second contact.

10. The feminine product transport apparatus of claim 1, additionally comprising:

said sensor connected with each said recess is comprised of a first switch positioned at a first end of said recess and a second switch positioned at an opposite end of said recess;

said first switch having a first contact which projects into said recess and a second contact positioned within said carrier;

said second switch having a first contact which projects into said recess and a second contact positioned within said carrier; and said occupancy signal generated when a said tampon located in said recess deflects either said first contact of said first switch into a first electrical contact with said second contact of said first switch, or said first contact of said second switch into a second electrical contact with said second contact of said second switch.

11. The feminine product transport apparatus of claim 1, additionally comprising:

ordering software running on said computing device of said user, said ordering software operating to the task of communicating over a network to which said computing device of said user is engaged, to order tampons for delivery to said user.

\* \* \* \* \*